(12) United States Patent
Getto et al.

(10) Patent No.: US 9,412,166 B2
(45) Date of Patent: Aug. 9, 2016

(54) GENERATING THREE DIMENSIONAL DIGITAL DENTITION MODELS FROM SURFACE AND VOLUME SCAN DATA

(75) Inventors: Phillip Getto, Plano, TX (US); Rohit Sachdeva, Plano, TX (US); Peer Sporbert, Berlin (DE); Markus Kaufmann, Berlin (DE)

(73) Assignee: ORAMETRIX, INC., Richardson, TX (US)

( * ) Notice: Subject to any disclaimer, the term of this patent is extended or adjusted under 35 U.S.C. 154(b) by 248 days.

(21) Appl. No.: 12/772,208

(22) Filed: May 1, 2010

(65) Prior Publication Data

US 2011/0268327 A1 Nov. 3, 2011

(51) Int. Cl.
*G06T 7/00* (2006.01)
*G09B 23/28* (2006.01)
*A61B 6/14* (2006.01)

(52) U.S. Cl.
CPC ............ *G06T 7/0024* (2013.01); *G09B 23/283* (2013.01); *A61B 6/14* (2013.01); *G06T 2207/10028* (2013.01); *G06T 2207/10081* (2013.01); *G06T 2207/10088* (2013.01); *G06T 2207/10116* (2013.01); *G06T 2207/30036* (2013.01)

(58) Field of Classification Search
CPC .............. G06T 7/0012; G06T 7/0024; G06T 2207/30036; A61B 6/5229; A61B 6/5247; A61B 9/0046; A61B 9/0053; A61B 13/0004
See application file for complete search history.

(56) References Cited

U.S. PATENT DOCUMENTS

| 6,632,089 B2* | 10/2003 | Rubbert et al. .................. 433/24 |
| 6,648,640 B2* | 11/2003 | Rubbert et al. .................. 433/24 |
| 6,845,175 B2* | 1/2005 | Kopelman et al. ............ 382/154 |
| 6,947,038 B1* | 9/2005 | Anh et al. ...................... 345/419 |
| 7,027,642 B2* | 4/2006 | Rubbert et al. ................ 382/154 |
| 7,068,825 B2* | 6/2006 | Rubbert et al. ................ 382/128 |
| 7,080,979 B2* | 7/2006 | Rubbert et al. .................. 433/24 |
| 7,234,937 B2* | 6/2007 | Sachdeva et al. ................ 433/24 |
| 7,717,708 B2* | 5/2010 | Sachdeva et al. ................ 433/24 |
| 2009/0316966 A1* | 12/2009 | Marshall et al. .............. 382/128 |

OTHER PUBLICATIONS

Nkenke et al. (Jul. 2004) "Fusion of computed tomography data and optical 3D images of the dentition for streak artifact correction in the simulation of orthognathic surgery." Dentomaxillofacial Radiology, vol. 33 pp. 226-232.*

PerkinElmer, Inc. (2001) "1100 Series FX-1160 Datasheet."*

Uechi et al. (2006) "A novel method for the 3-dimensional simulation of orthognathic surgery by using a multimodal image fusion technique." Am. J. of Orthodontics and Dentofacial Orthopedics, vol. 130 No. 6, pp. 786-798.*

* cited by examiner

*Primary Examiner* — Andrew W Johns
(74) *Attorney, Agent, or Firm* — Jasvantrai C. Shah

(57) ABSTRACT

A method and apparatus are disclosed enabling an orthodontist or a user to create an integrated three dimensional digital model of dentition and surrounding anatomy of an orthodontic patient from a three-dimensional digital model obtained using a scanner with a three-dimensional digital model obtained using a Cone Beam Computed Tomography (CBCT) or Magnetic Resonance Tomography (MRT) imaging devices. The digital data obtained from scanning as well as from CBCT imaging are downloaded into a computer workstation, and registered together in order to create a comprehensive 3-D model of the patient's teeth with roots, bones and soft tissues. The invention provides substantial improvement over the traditional two dimensional imaging modalities such as x-rays, photographs, cephalometric tracing for diagnosis and treatment planning.

20 Claims, 14 Drawing Sheets

GENERATING THREE DIMENSIONAL DIGITAL DENTITION MODELS FROM SURFACE AND VOLUME SCAN DATA

CROSS-REFERENCE TO RELATED APPLICATIONS

This application is related to the following applications.

application Ser. No. 09/834,593, filed Apr. 13, 2001, now issued as U.S. Pat. No. 7,068,825;

application Ser. No. 09/835,007, filed Apr. 13, 2001, now issued as U.S. Pat. No. 7,027,642;

application Ser. No. 09/834,413, filed Apr. 13, 2001, now issued as U.S. Pat. No. 7,080,979;

application Ser. No. 09/835,039, filed Apr. 13, 2001, now issued as U.S. Pat. No. 6,648,640;

application Ser. No. 09/834,593, filed Apr. 13, 2001, now issued as U.S. Pat. No. 7,068,825;

application Ser. No. 10/429,123, filed May 2, 2003, now issued as U.S. Pat. No. 7,234,937; and application Ser. No. 10/428,461, filed May 2, 2003, now issued as U.S. Pat. No. 7,717,708, which is a continuation-in-part of application Ser. No. 09/834,412, filed Apr. 13, 2001, now issued as U.S. Pat. No. 6,632,089.

The entire contents of each of the above listed patent application are incorporated by reference herein.

BACKGROUND OF THE INVENTION

A. Field of the Invention

This invention relates generally to the field of orthodontics. More particularly, the invention relates to generating three dimensional models of the dentition of a patient from surface scanning and volume scanning data.

B. Description of Related Art

In orthodontics, a patient suffering from a malocclusion is typically treated by bonding brackets to the surface of the patient's teeth. The brackets have slots for receiving an archwire. The bracket-archwire interaction governs forces applied to the teeth and defines the desired direction of tooth movement. Typically, the bends in the wire are made manually by the orthodontist. During the course of treatment, the movement of the teeth is monitored. Corrections to the bracket position and/or wire shape are made manually by the orthodontist.

The key to efficiency in treatment and maximum quality in results is a realistic simulation of the treatment process. Today's orthodontists have the possibility of taking plaster models of the upper and lower jaw, cutting the model into single tooth models and sticking these tooth models into a wax bed, lining them up in the desired position, the so-called set-up. This approach allows for reaching a perfect occlusion without any guessing. The next step is to bond a bracket at every tooth model. This would tell the orthodontist the geometry of the wire to run through the bracket slots to receive exactly this result. The next step involves the transfer of the bracket position to the original malocclusion model. To make sure that the brackets will be bonded at exactly this position at the real patient's teeth, small templates for every tooth would have to be fabricated that fit over the bracket and a relevant part of the tooth and allow for reliable placement of the bracket on the patient's teeth. To increase efficiency of the bonding process, another option would be to place each single bracket onto a model of the malocclusion and then fabricate one single transfer tray per jaw that covers all brackets and relevant portions of every tooth. Using such a transfer tray guarantees a very quick and yet precise bonding using indirect bonding.

However, it is obvious that such an approach requires an extreme amount of time and labor and thus is too costly, and this is the reason why it is not practiced widely. The normal orthodontist does not fabricate set-ups; he places the brackets directly on the patient's teeth to the best of his knowledge, uses an off-the-shelf wire and hopes for the best. There is no way to confirm whether the brackets are placed correctly; and misplacement of the bracket will change the direction and/or magnitude of the forces imparted on the teeth. While at the beginning of treatment things generally run well as all teeth start to move at least into the right direction, at the end of treatment a lot of time is lost by adaptations and corrections required due to the fact that the end result has not been properly planned at any point of time. For the orthodontist this is still preferable over the lab process described above, as the efforts for the lab process would still exceed the efforts that he has to put in during treatment. And the patient has no choice and does not know that treatment time could be significantly reduced if proper planning was done.

U.S. Pat. No. 5,431,562 to Andreiko et al. describes a computerized, appliance-driven approach to orthodontics. In this method, first certain shape information of teeth is acquired. A uniplanar target archform is calculated from the shape information. The shape of customized bracket slots, the bracket base, and the shape of an orthodontic archwire, are calculated in accordance with a mathematically-derived target archform. The goal of the Andreiko et al. method is to give more predictability, standardization, and certainty to orthodontics by replacing the human element in orthodontic appliance design with a deterministic, mathematical computation of a target archform and appliance design. Hence the '562 patent teaches away from an interactive, computer-based system in which the orthodontist remains fully involved in patient diagnosis, appliance design, and treatment planning and monitoring.

More recently, in the late 1990's Align Technologies began offering transparent, removable aligning devices as a new treatment modality in orthodontics. In this system, a plaster model of the dentition of the patent is obtained by the orthodontist and shipped to a remote appliance manufacturing center, where it is scanned with a laser. A computer model of the dentition in a target situation is generated at the appliance manufacturing center and made available for viewing to the orthodontist over the Internet. The orthodontist indicates changes they wish to make to individual tooth positions. Later, another virtual model is provided over the Internet and the orthodontist reviews the revised model, and indicates any further changes. After several such iterations, the target situation is agreed upon. A series of removable aligning devices or shells are manufactured and delivered to the orthodontist. The shells, in theory, will move the patient's teeth to the desired or target position.

U.S. Pat. No. 6,632,089 to Rubbert discloses an interactive, software-based treatment planning method to correct a malocclusio. The method can be performed on an orthodontic workstation in a clinic or at a remote location such as a lab or precision appliance manufacturing center. The workstation stores a virtual three-dimensional model of the dentition of a patient and patient records. The virtual model is manipulated by the user to define a target situation for the patient, including a target archform and individual tooth positions in the archform. Parameters for an orthodontic appliance, such as the location of orthodontic brackets and resulting shape of a customized orthodontic archwire, are obtained from the simulation of tooth movement to the target situation and the placement position of virtual brackets.

In orthodontic treatment planning, virtual models of the dentition of a patient play a key role and are extremely important. By-and-large so far the models created from surface scan are used. These models lack in the areas or roots, bones and soft tissues. Therefore a need exists to for the virtual three dimensional models of dentition and surrounding anatomy which can be used in planning orthodontic treatment. The present invention meets this need.

SUMMARY OF THE INVENTION

Surface scans of a patient's dentition are obtained using in-vivo scanning or other types of scanning such as scanning an impression of the patient's dentition or scanning a physical model of the patient's dentition. There are number of scanning devices available to accomplish this task. Volume scans of the patient's dentition are obtained using Cone Beam Computed tomography (CBCT) or Magnetic Resonent Tomography (MRT) imaging equipment. Surface scans provide data for modeling basically tooth crowns; whereas volume scans provide data for crowns as well as roots, bones, soft tissues and airways. The invention disclosed herein combines the surface scan data with the volume scan data to generate three dimensional models of a patient's dentition and surrounding anatomy including roots, bones, soft tissues, airways, etc. Both method and workstation for generating these virtual models are disclosed. The procedure can be summarized as follows:

a. obtain a intraoral surface scan or impression/plaster scan of a part or the dentition within the jaw of a patient;

b. obtain volume scan of the same patient's dentition including roots, bones, soft tissues, etc.

Note: both types of scans, i.e., surface and volume, have to represent the same patient in the same or similar condition.

c. generate a surface representation of the dentition from a the volume scan.

The surface representation can be generated by thresh-holding or by any other method to generate a surface from volume data. The scan data is processed to produce a mesh.

d. register the whole or a part of the surface scan into the surface extracted from volume scan data. This scan a\data is also processed to produce a mesh. The precondition for the registration is that an overlap between both types of scans, i.e., surface and volume, must exist that is sufficiently similar in both scans.

e. merging both meshes together, so that the data from the surface scan replaces the data built from the volume scan.

The workstation receives both types of scanning data and provides software tools for processing each type of data as well as for merging them together. The results are displayed on the workstation display.

BRIEF DESCRIPTION OF THE DRAWINGS

Presently preferred embodiments of the invention are described below in reference to the appended drawings, wherein like reference numerals refer to like elements in the various views, and in which:

FIG. 2 shows a slice from a CBCT scan of a patient's dentition. Also shown in this figure is a photographic view of a tooth with a metal filling that distorts the CBCT data.

FIG. 3 shows a volume scan from CBCT imaging of the patient's dentition. Also shown is the same tooth with a metal filling previously shown in FIG. 2.

FIG. 4 shows a volume scan from CBCT with noise caused by slight movement of the dentition by the patient while scanning was in progress.

FIG. 5 shows a side view of both jaws of a patient with teeth, roots and jaw bones of the dentition of the patient developed from the CBCT volume scan data.

FIG. 6 shows a front view of both jaws of the patient with teeth, roots and jaw bones of the dentition of the patient developed from the CBCT volume scan data. The brackets placed on the patient's teeth are shown as well.

FIG. 7 shows surface scan data of the partial dentition of a patient. Also shown is the same tooth with a metal filling previously shown in FIG. 2.

FIG. 8 shows final modeling of teeth obtained from surface scanning of the dentition of a patient. While tooth crowns are displayed in the model, tooth roots and jaw bones are missing.

FIG. 9 shows a part of the surface scan data previously shown in FIG. 7 super imposed over the volume scan data previously shown in FIG. 3. Also shown is the same tooth with a metal filling previously shown in FIG. 2.

FIG. 10 shows another example of a part of surface scan data super imposed over volume scan data. Also shown in this figure is a photographic view of the mouth of the patient that was scanned.

FIG. 11 shows a finished model of the teeth with roots of a patient obtained by registering the mesh data from the surface scan with the mesh data from the volume scan of the dentition of a patient.

FIGS. 12 and 13 show different views of the teeth model shown in FIG. 11.

FIG. 14 shows the three-dimensional final model teeth with brackets placed on the teeth.

DETAILED DESCRIPTION OF PREFERRED EMBODIMENT

Before describing the features of this invention in detail, an overview of a unified workstation will be set forth initially. The workstation provides software features that create two dimensional and/or three-dimensional virtual patient model on a computer, which can be used for purposes of treatment planning in accordance with a presently preferred embodiment.

Many of the details and computer user interface tools which a practitioner may use in adjusting tooth position, designing appliance shape and location, managing space between teeth, and arriving at a finish tooth position using interaction with a computer storing and displaying a virtual model of teeth are set forth in the prior application Ser. No. 09/834,412 filed Apr. 13, 2001, and in published OraMetrix patent application WO 01/80761, the contents of which are incorporated by reference herein. Other suites of tools and functions are possible and within the scope of the invention. Such details will therefore be omitted from the present discussion.

General Description

A unified workstation environment and computer system for diagnosis, treatment planning and delivery of therapeutics, especially adapted for treatment of craniofacial structures, is described below. In one possible example, the system is particularly useful in diagnosis and planning treatment of an orthodontic patient. Persons skilled in the art will understand that the invention, in its broader aspects, is applicable to other craniofacial disorders or conditions requiring surgery, prosthodontic treatment, restorative treatment, etc.

Figure 1:
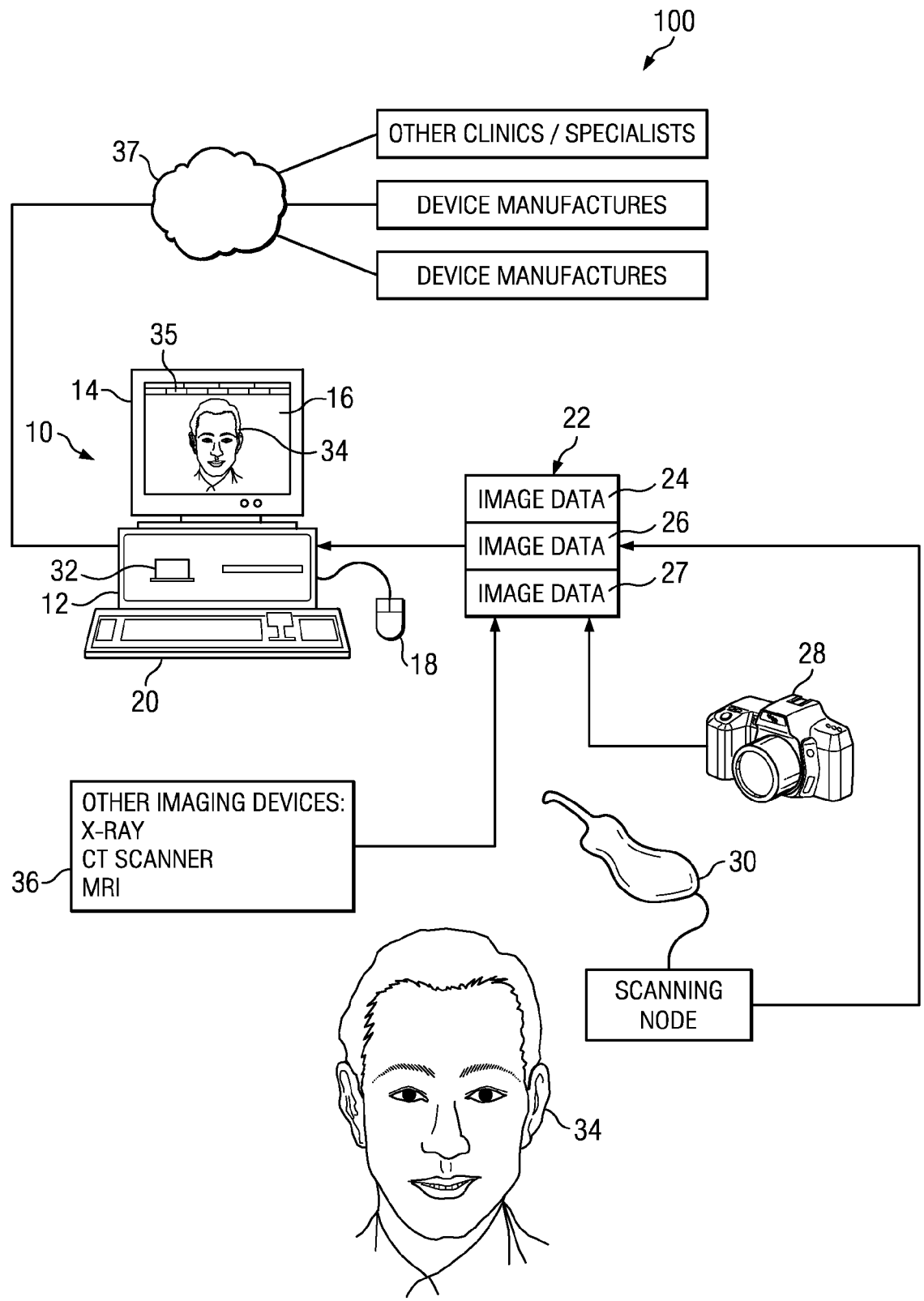
FIG. 1 is block diagram of a system for creating a three-dimensional virtual patient model and for diagnosis and planning treatment of the patient.

A presently preferred embodiment is depicted in FIG. 1. The overall system 100 includes a general-purpose computer system 10 having a processor (CPU 12) and a user interface 14, including screen display 16, mouse 18 and keyboard 20. The system is useful for planning treatment for a patient 34.

The system 100 includes a computer storage medium or memory 22 accessible to the general-purpose computer system 10. The memory 22, such as a hard disk memory or attached peripheral devices, stores two or more sets of digital data representing patient craniofacial image information. These sets include at least a first set of digital data 24 representing patient craniofacial image information obtained from a first imaging device and a second set of digital data 26 representing patient craniofacial image information obtained from a second image device different from the first image device. The first and second sets of data represent, at least in part, common craniofacial anatomical structures of the patient. At least one of the first and second sets of digital data normally would include data representing the external visual appearance or surface configuration of the face of the patient.

In a representative and non-limiting example of the data sets, the first data set 24 could be a set of two dimensional color photographs of the face and head of the patient obtained via a color digital camera 28, and the second data set is three-dimensional image information of the patient's teeth, acquired via a suitable scanner 30, such as a hand-held optical 3D scanner, or other type of scanner. The memory 22 may also store other sets 27 of digital image data, including digitized X-rays, MRI or ultrasound images, CT scanner etc., from other imaging devices 36. The other imaging devices need not be located at the location or site of the workstation system 100. Rather, the imaging of the patient 34 with one or other imaging devices 36 could be performed in a remotely located clinic or hospital, in which case the image data is obtained by the workstation 100 over the Internet 37 or some other communications medium, and stored in the memory 22.

The system 100 further includes a set of computer instructions stored on a machine-readable storage medium. The instructions may be stored in the memory 22 accessible to the general-purpose computer system 10. The machine-readable medium storing the instructions may alternatively be a hard disk memory 32 for the computer system 10, external memory devices, or may be resident on a file server on a network connected to the computer system, the details of which are not important. The set of instructions, described in more detail below, comprise instructions for causing the general computer system 10 to perform several functions related to the generation and use of the virtual patient model in diagnostics, therapeutics and treatment planning.

These functions include a function of automatically, and/or with the aid of operator interaction via the user interface 14, superimposing the first set 24 of digital data and the second set 26 of digital data so as to provide a composite, combined digital representation of the craniofacial anatomical structures in a common coordinate system. This composite, combined digital representation is referred to herein occasionally as the "virtual patient model," shown on the display 16 of FIG. 1 as a digital model of the patient 34. Preferably, one of the sets 24, 26 of data includes photographic image data of the patient's face, teeth and head, obtained with the color digital camera 28. The other set of data could be intra-oral 3D scan data obtained from the hand-held scanner 30, CT scan data, X-Ray data, MRI, etc. In the example of FIG. 1, the hand-held scanner 30 acquires a series of images containing 3D information and this information is used to generate a 3D model in the scanning node 31, in accordance with the teachings of the published PCT application of OraMetrix, PCT publication no. WO 01/80761, the content of which is incorporated by reference herein. Additional data sets are possible, and may be preferred in most embodiments. For example the virtual patient model could be created by a superposition of the following data sets: intra-oral scan of the patient's teeth, gums, and associated tissues, X-Ray, CT scan, intra-oral color photographs of the teeth to add true color (texture) to the 3D teeth models, and color photographs of the face, that are combined in the computer to form a 3D morphable face model. These data sets are superimposed with each other, with appropriate scaling as necessary to place them in registry with each other and at the same scale. The resulting representation can be stored as a 3D point cloud representing not only the surface on the patient but also interior structures, such as tooth roots, bone, and other structures. In one possible embodiment, the hand-held in-vivo scanning device is used which also incorporates a color CCD camera to capture either individual images or video.

The software instructions further includes a set of functions or routines that cause the user interface 16 to display the composite, combined digital three-dimensional representation of craniofacial anatomical structures to a user of the system. In a representative embodiment, computer-aided design (CAD)-type software tools are used to display the model to the user and provide the user with tools for viewing and studying the model. Preferably, the model is cable of being viewed in any orientation. Tools are provided for showing slices or sections through the model at arbitrary, user defined planes. Alternatively, the composite digital representation may be printed out on a printer or otherwise provided to the user in a visual form.

The software instructions further include instructions that, when executed, provide the user with tools on the user interface 14 for visually studying, on the user interface, the interaction of the craniofacial anatomical structures and their relationship to the external, visual appearance of the patient. For example, the tools include tools for simulating changes in the anatomical position or shape of the craniofacial anatomical structures, e.g., teeth, jaw, bone or soft tissue structure, and their effect on the external, visual appearance of the patient. The preferred aspects of the software tools include tools for manipulating various parameters such as the age of the patient; the position, orientation, color and texture of the teeth; reflectivity and ambient conditions of light and its effect on visual appearance. The elements of the craniofacial and dental complex can be analyzed quickly in either static format (i.e., no movement of the anatomical structures relative to each other) or in an dynamic format (i.e., during movement of anatomical structures relative to each other, such as chewing, occlusion, growth, etc.). To facilitate such modeling and simulations, teeth may be modeled as independent, individually moveable 3 dimensional virtual objects, using the techniques described in the above-referenced OraMetrix published PCT application, WO 01/80761.

The workstation environment provided by this invention provides a powerful system and for purposes of diagnosis, treatment planning and delivery of therapeutics. For example, the effect of jaw and skull movement on the patient's face and smile can be studied. Similarly, the model can be manipulated to arrive at the patient's desired feature and smile. From this model, and more particularly, from the location and position of individual anatomical structures (e.g., individual tooth positions and orientation, shape of arch and position of upper and lower arches relative to each other), it is possible to automatically back solve for or derive the jaw, tooth, bone and/or soft tissue corrections that must be applied to the patient's initial, pre-treatment position to provide the desired result. This leads directly to a patient treatment plan.

These simulation tools, in a preferred embodiment, comprise user-friendly and intuitive icons 35 that are activated by a mouse or keyboard on the user interface of the computer system 10. When these icons are activated, the software instruction provide pop-up, menu, or other types screens that enable a user to navigate through particular tasks to highlight and select individual anatomical features, change their positions relative to other structures, and simulate movement of the jaws (chewing or occlusion). Examples of the types of navigational tools, icons and treatment planning tools for a computer user interface that may be useful in this process and provide a point of departure for further types of displays useful in this invention are described in the patent application of Rudger Rubbert et al., Ser. No. 09/835,039 filed Apr. 13, 2001, the contents of which are incorporated by reference herein.

The virtual patient model, or some portion thereof, such as data describing a three-dimensional model of the teeth in initial and target or treatment positions, is useful information for generating customized orthodontic appliances for treatment of the patient. The position of the teeth in the initial and desired positions can be used to generate a set of customized brackets, and customized flat planar archwire, and customized bracket placement jigs, as described in the above-referenced Andreiko et al. patents. Alternatively, the initial and final tooth positions can be used to derive data sets representing intermediate tooth positions, which are used to fabricate transparent aligning shells for moving teeth to the final position, as described in the above-referenced Chisti et al. patents. The data can also be used to place brackets and design a customized archwire as described in the previously cited application Ser. No. 09/835,039.

To facilitate sharing of the virtual patient model among specialists and device manufacturers, the system 100 includes software routines and appropriate hardware devices for transmitting the virtual patient model or some subset thereof over a computer network. The system's software instructions are preferably integrated with a patient management program having a scheduling feature for scheduling appointments for the patient. The patient management program provides a flexible scheduling of patient appointments based on progress of treatment of the craniofacial anatomical structures. The progress of treatment can be quantified. The progress of treatment can be monitored by periodically obtaining updated three-dimensional information regarding the progress of treatment of the craniofacial features of the patient, such as by obtaining updated scans of the patient and comparison of the resulting 3D model with the original 3D model of the patient prior to initiation of treatment.

Thus, it is contemplated that system described herein provides a set of tools and data acquisition and processing subsystems that together provides a flexible, open platform or portal to a variety of possible therapies and treatment modalities, depending on the preference of the patient and the practitioner. For example, a practitioner viewing the model and using the treatment planning tools may determine that a patient may benefit from a combination of customized orthodontic brackets and wires and removable aligning devices. Data from the virtual patient models is provided to diverse manufacturers for coordinated preparation of customized appliances. Moreover, the virtual patient model and powerful tools described herein provide a means by which the complete picture of the patient can be shared with other specialists (e.g., dentists, maxilla-facial or oral surgeons, cosmetic surgeons, other orthodontists) greatly enhancing the ability of diverse specialists to coordinate and apply a diverse range of treatments to achieve a desired outcome for the patient. In particular, the overlay or superposition of a variety of image information, including 2D X-Ray, 3D teeth image data, photographic data, CT scan data, and other data, and the ability to toggle back and forth between these views and simulate changes in position or shape of craniofacial structures, and the ability to share this virtual patient model across existing computer networks to other specialists and device manufacturers, allows the entire treatment of the patient to be simulated and modeled in a computer. Furthermore, the expected results can be displayed before hand to the patient and changes made depending on the patient input.

With the above general description in mind, additional details of presently preferred components and aspects of the inventive system and the software modules providing the functions referenced above will be described next.

Integrated 3-D Modeling of Patient's Dentition from Surface Scanning and CBCT Imaging The invention disclosed herein enables orthodontists to accurately measure complex three dimensional anatomy during diagnosis and treatment planning of orthodontic patients. The invention enables orthodontists or users to capture 3D scans with intraoral scanners as well as cone beam computed tomography (CBCT) that can capture highly precise digital scans. The resulting digital images are downloaded to a computer, and combined in order to create comprehensive 3-D models of the patient's dentition, roots, bones and soft tissues thereby creating 3-D digital teeth model and surrounding anatomy of pre-treatment mouth. The invention provides substantial improvement over the traditional two dimensional imaging modalities such as x-rays, photographs, cephalometric tracing for diagnosis and treatment planning.

In a preferred embodiment of the invention, scanning is done in-vivo using a white light scanner, and is non-invasive. Scanner is reference independent, so the object being scanned can move while being scanned and the scanned data will still be useful. Scanning can be performed again to get the modeling information that might be missing. In order to perform bite registration, it does not require wax bite. This type of scanning does not allow reconstruction of data. Pano and Ceph should be taken separately and imported into the image management software.

When needed, a partial scan can be taken. The scanning captures only the coronal portion of the tooth in 3-D. However, gingiva is viewable with this type of scanning. Scanning can be performed with orthodontic brackets, made of either plastic or metal or a combination, placed on the patient's teeth; as well as with one or more teeth crowns having metal fillings. Tooth separators are not required in order to perform scanning. Excessive voids in scan data can affect tooth modeling. This type of scanning can be used for creating 3D models of teeth from raw scan data for diagnostic, therapeutic and final outcome evaluation.

In contrast, CBCT imaging is invasive, and requires tooth separators. In order to perform bite registration, a wax bite or bite block is required. Multiple slices taken by CBCT can be reconstructed to look like 3-D images of teeth, jaws and even soft tissue; and Pano and Ceph can also be reconstructed from the data captured by CBCT. Partial scan is not possible with CBCT. CBCT images capture crown, root, surrounding bone and soft tissues which can be put together in three dimensions. Although gingiva can be viewed with CBCT images, the root anatomy obtained is preferred. There are several limitations while using CBCT for imaging the patient's dentition, such as for example, (a) the brackets are limited generally to plastic brackets since metal brackets cause image distortion, (b) metal crown fillings by-and-large cannot be handled since fillings larger than 4 mm creates noise causing image distortion and (c) a patient cannot move during the CBCT imaging procedure since any motion during imaging causes blurring of image making it unusable. Additionally, wax bite or bite blocks used as separators to prevent opposing teeth from coming in contact during the CBCT imaging procedure. Excessive 'noise' caused by large metal objects in patient's mouth causes distortion of images adversely affecting tooth modeling.

CBCT imaging can also be used for creating 3D models of teeth from raw image data for diagnostic, therapeutic and final outcome evaluation. Furthermore, X-rays can be reconstructed from CBCT images.

Surface scanning as well as volume scanning by CBCT or MRT imaging each has some short-comings. However, they can be used in a complimentary manner to produce 3-D digital models of patient's dentition including teeth with roots, bones and soft tissues such as gingival, and with excellent quality.

FIGS. 2-6 show data from the CBCT volume scan of a patient at different stages of processing.

Figure 2:
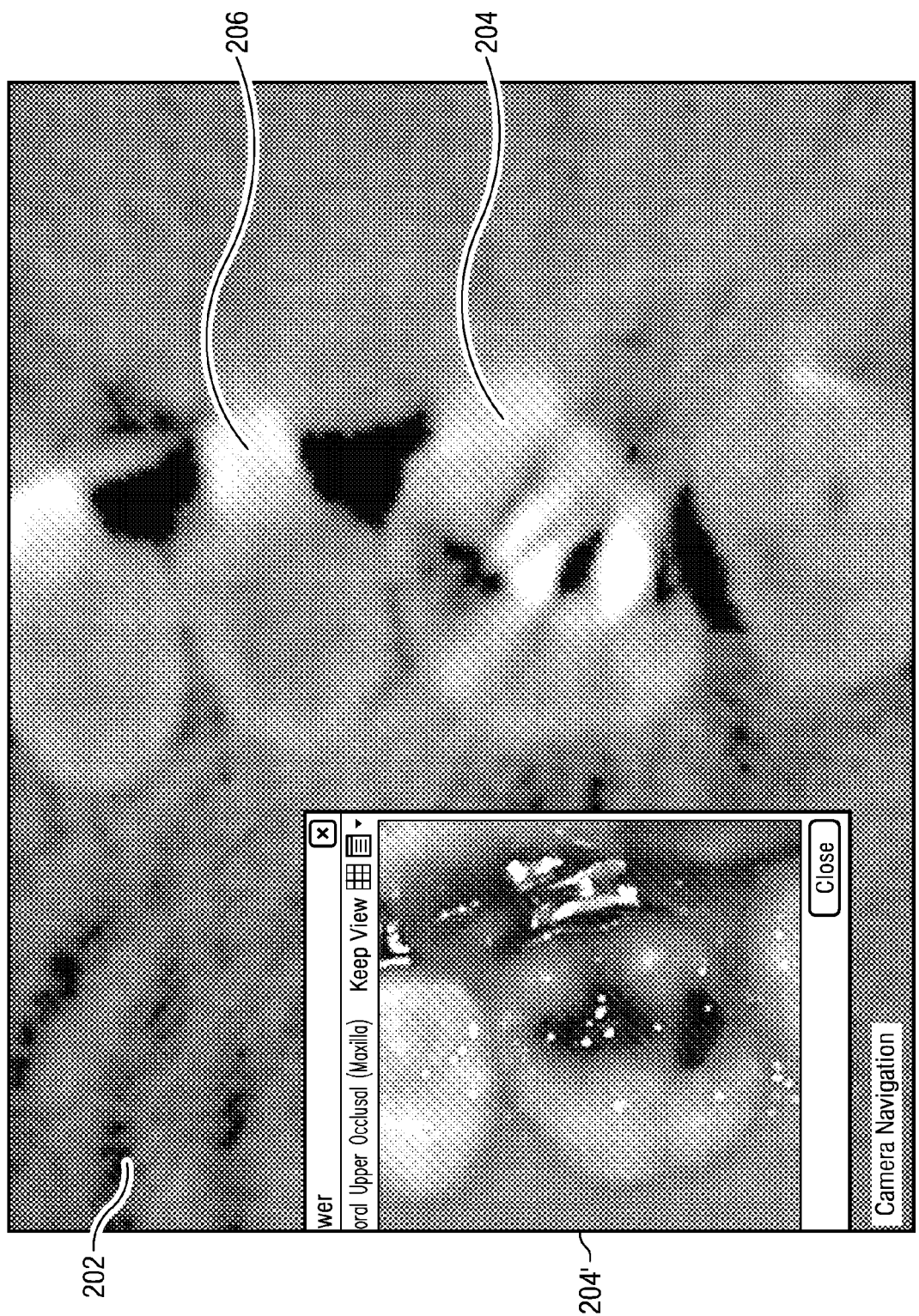
FIGS. 2-6 show data from the CBCT volume scan of a patient at different stages of processing.

FIG. 2 shows a slice 202 from a CBCT scan of a patient's dentition. Also shown in this figure is a photographic view of a tooth 204' with a metal filling that distorts the CBCT data. CBCT image 204 of tooth 204' is damaged in slice 202 due to the metal filling. Other teeth, for example image 206 of a tooth without metal filling comes out undamaged.

Figure 3:
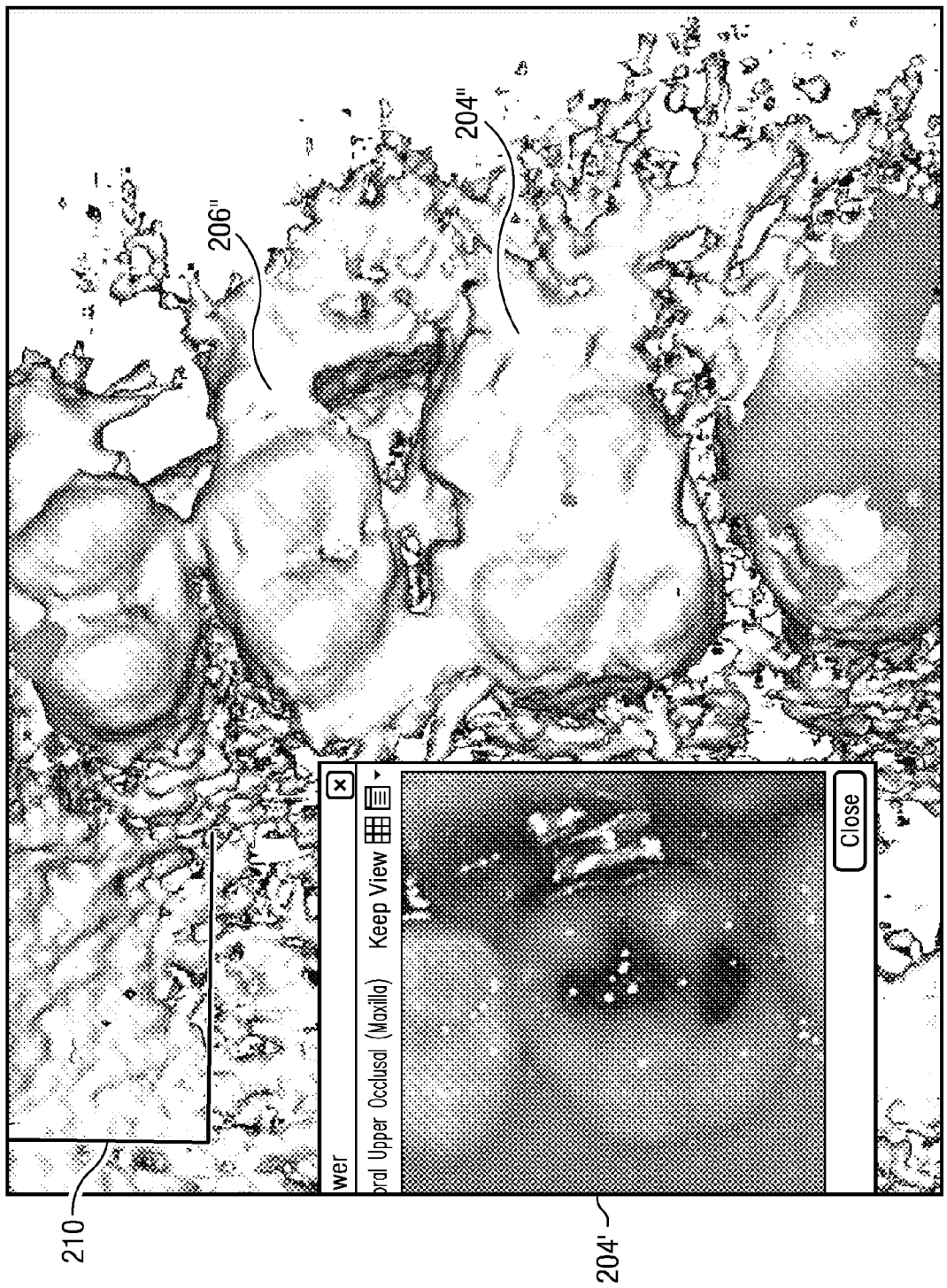

FIG. 3 shows a volume scan 210 from CBCT imaging of the patient's dentition. Also shown is the same tooth 204' with a metal filling previously shown in FIG. 2. The image 204" of the tooth 204' with the metal filling comes out damaged; whereas, image 206" of a tooth without metal filling is acceptable.

Figure 4:
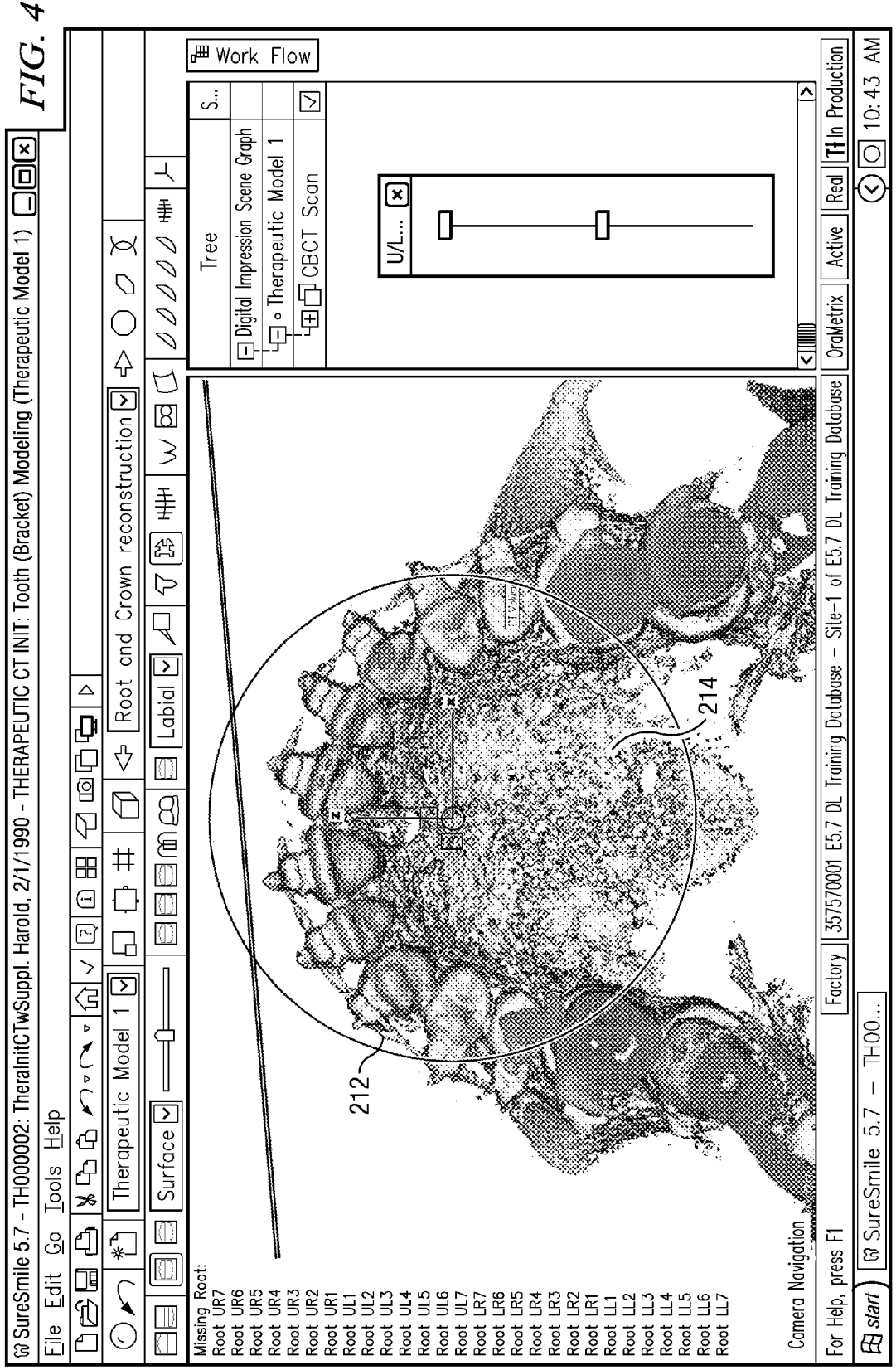

FIG. 4 shows a volume scan 212 from CBCT imaging with noise 214 caused by slight movement of the dentition by the patient while imaging was in progress.

Although other types of deficiencies are not shown by way of figures, one skilled in art would appreciate that volume scanning with CBCT or MRT has certain inherent disadvantages.

Figure 5:
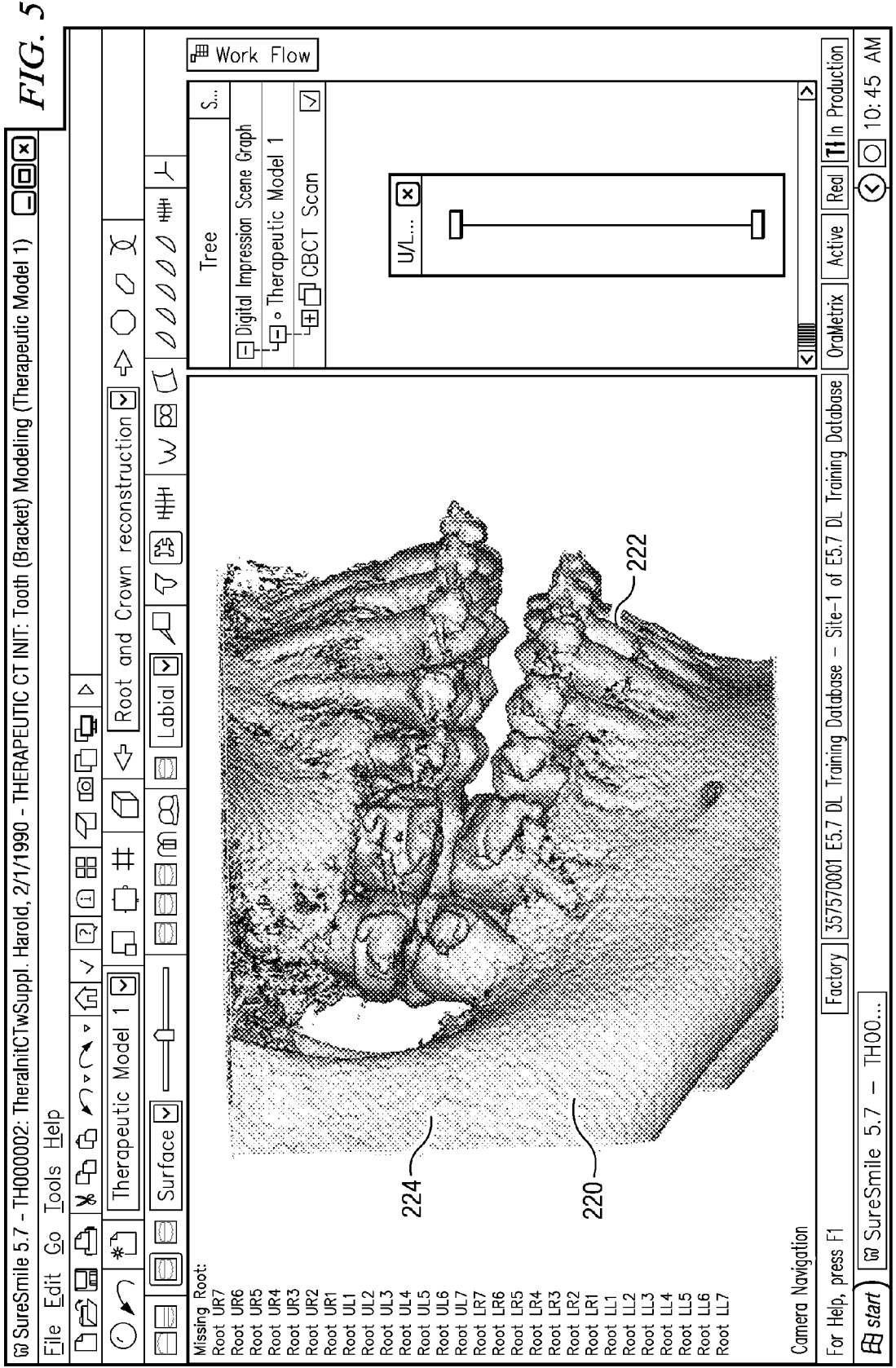

FIG. 5 shows a side view 220 of both jaws of a patient with teeth with roots 222 and jaw bones 224 of the dentition of the patient developed from the CBCT volume scan data.

Figure 6:
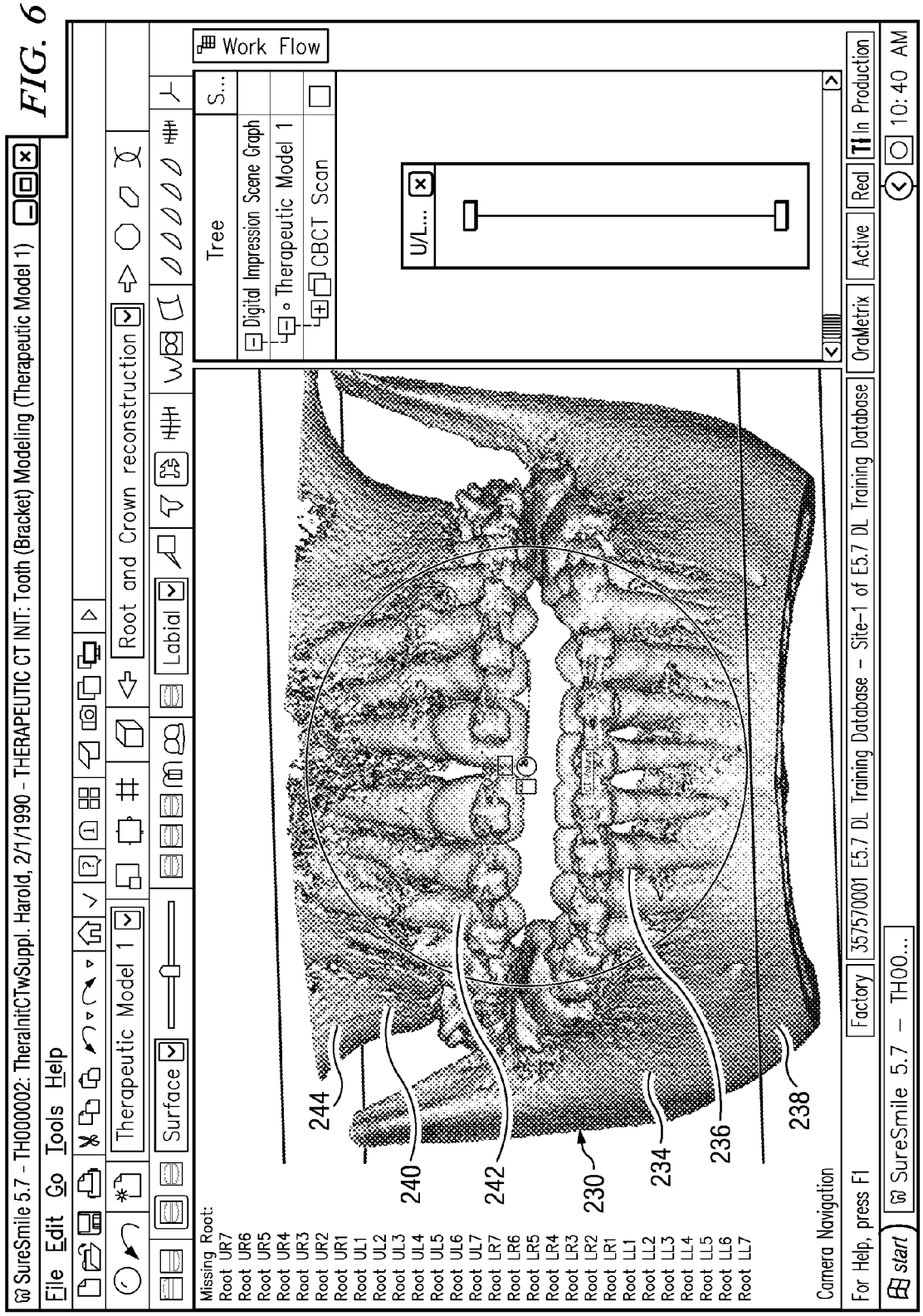

FIG. 6 shows a front view 230 of both jaws of the patient, lower jaw 234 and upper jaw 240, with teeth and roots 236 in the lower jaw and 242 in the upper jaw, and jaw bones 238 of the lower jaw and 244 of the upper jaw of the dentition of the patient developed from the CBCT volume scan data. The brackets placed on the patient's teeth are shown as well.

Figure 7:
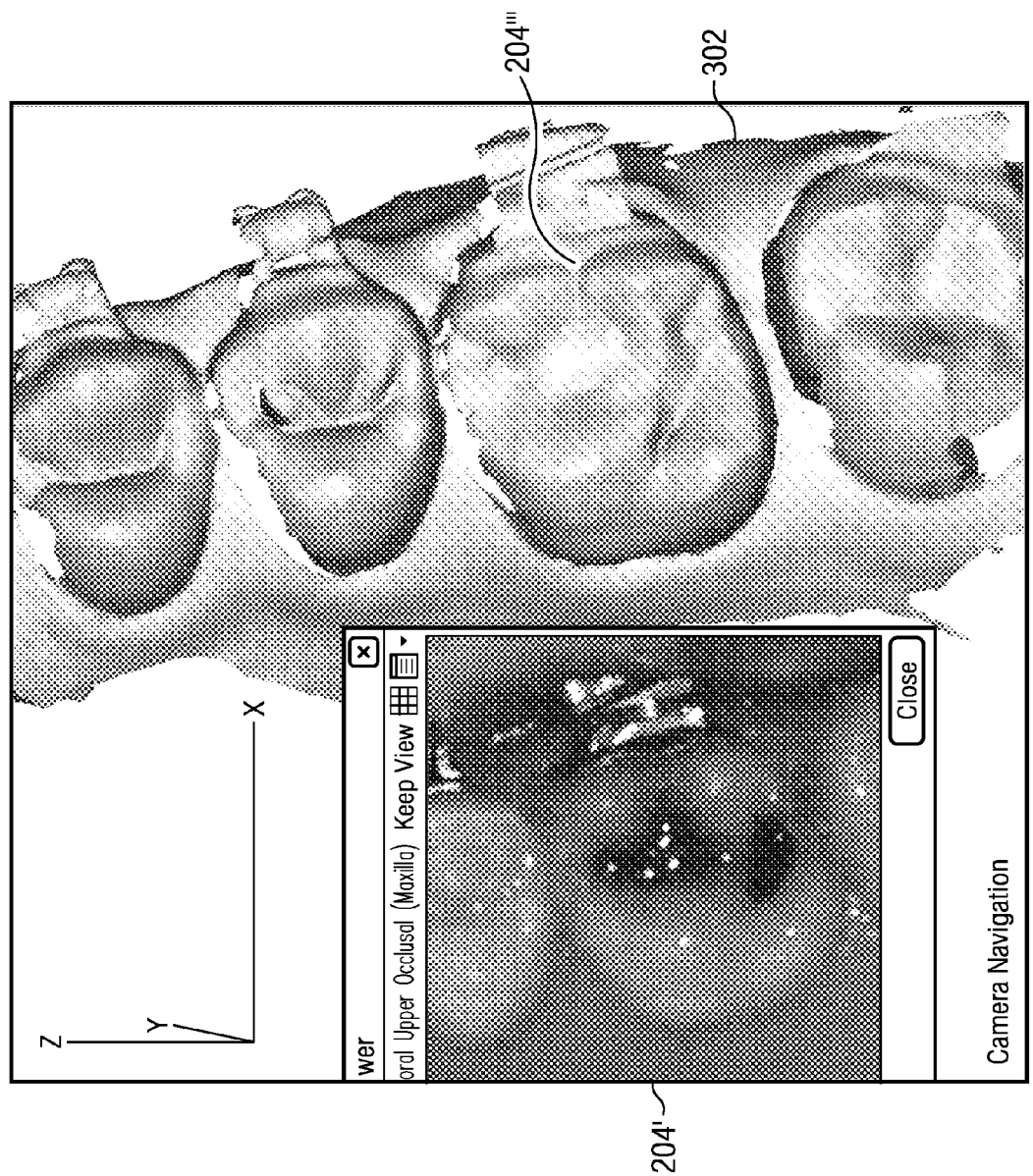
FIGS. 7-8 show data from surface scan of a patient at different stages of processing.
Figure 8:
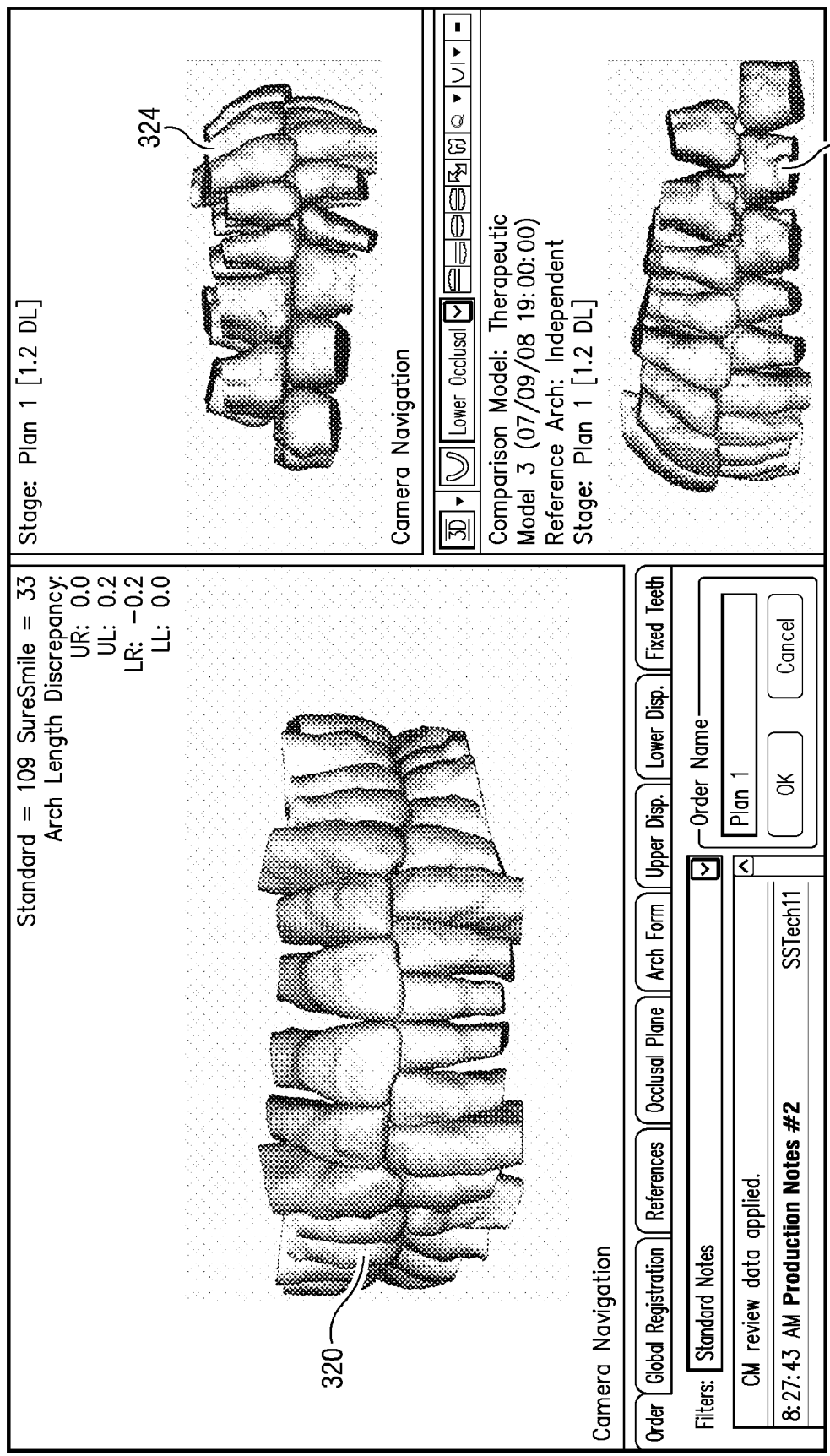

FIGS. 7-8 show data from surface scan of a patient at different stages of processing.

FIG. 7 shows surface scan 302 of the partial dentition of a patient. Also shown is the same tooth 204' with a metal filling previously shown in FIG. 2. Surface scan 204''' corresponding to tooth 204' is perfectly acceptable even thought the tooth has metal fillings.

FIG. 8 shows final modeling of teeth, in front view 320 and side views 324 and 328, obtained from surface scanning of the dentition of a patient. While tooth crowns are displayed in the model, tooth roots and jaw bones are missing.

FIGS. 9-14 show data from the CBCT volume scan of a patient being combined with the data from surface scan of the same patient at different stages of processing.

Figure 9:
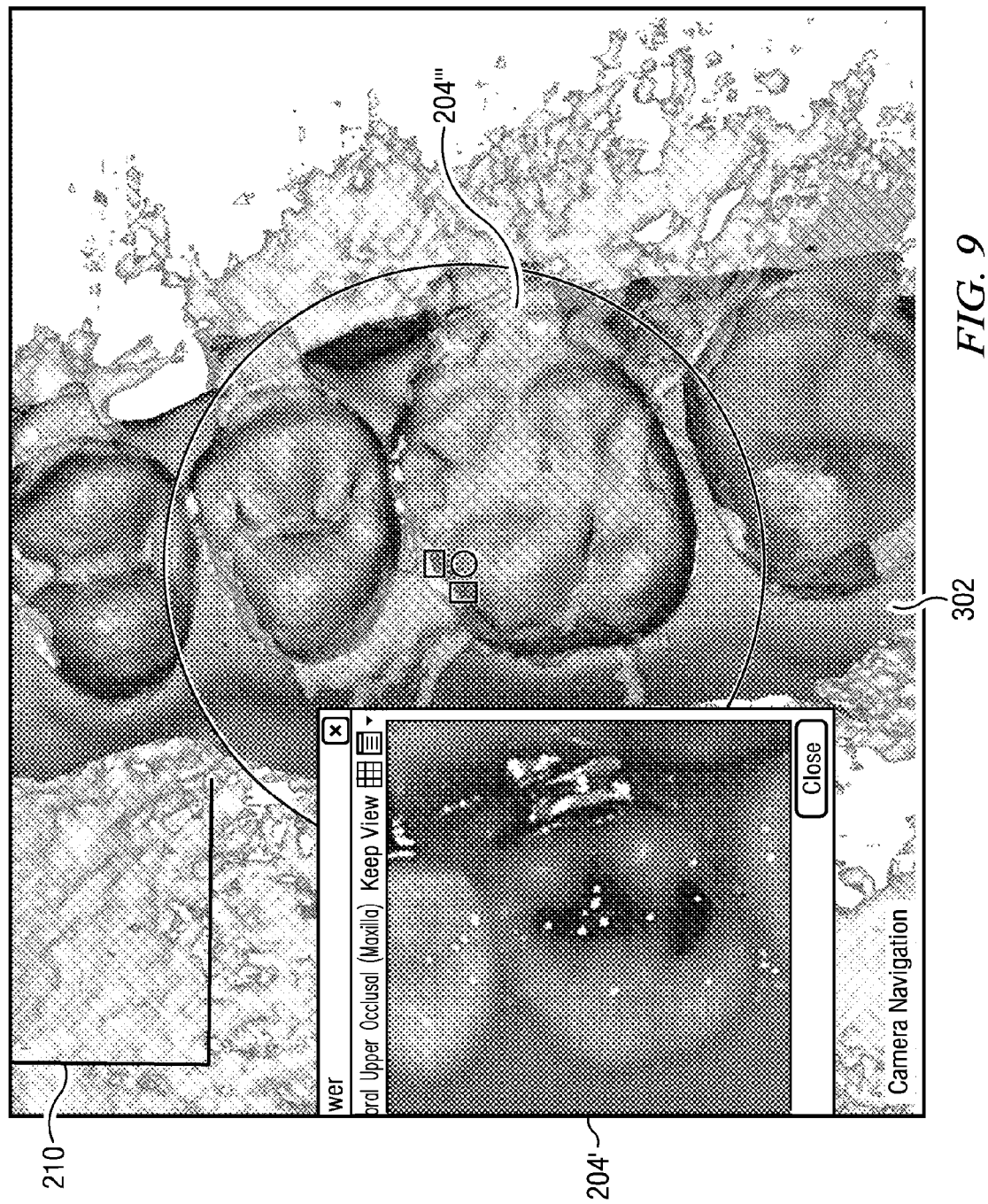
FIGS. 9-14 show data from the CBCT volume scan of a patient being combined with the data from surface scan of the same patient at different stages of processing.

FIG. 9 shows a part of the surface scan data 302 previously shown in FIG. 7 super imposed over the volume scan data 210 previously shown in FIG. 3. Also shown is the same tooth 204' with a metal filling previously shown in FIG. 2. Because of the surface scan data, tooth representation 204''' of tooth 204' is acceptable in this case.

Figure 10:
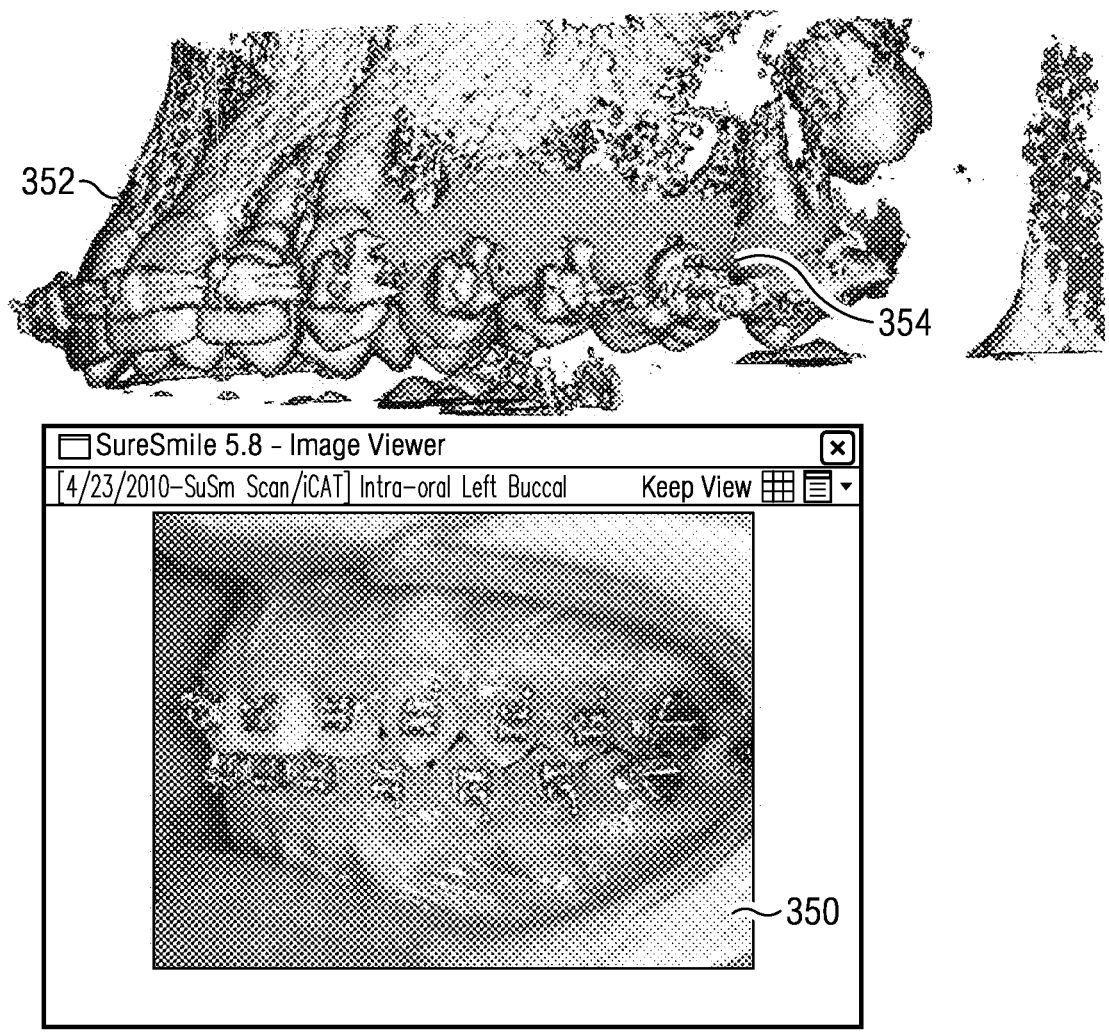

FIG. 10 shows another example 354 of a part of surface scan data super imposed over volume scan data 352. Also shown in this figure is a photographic view of the mouth 350 of the patient that was scanned.

Figure 11:
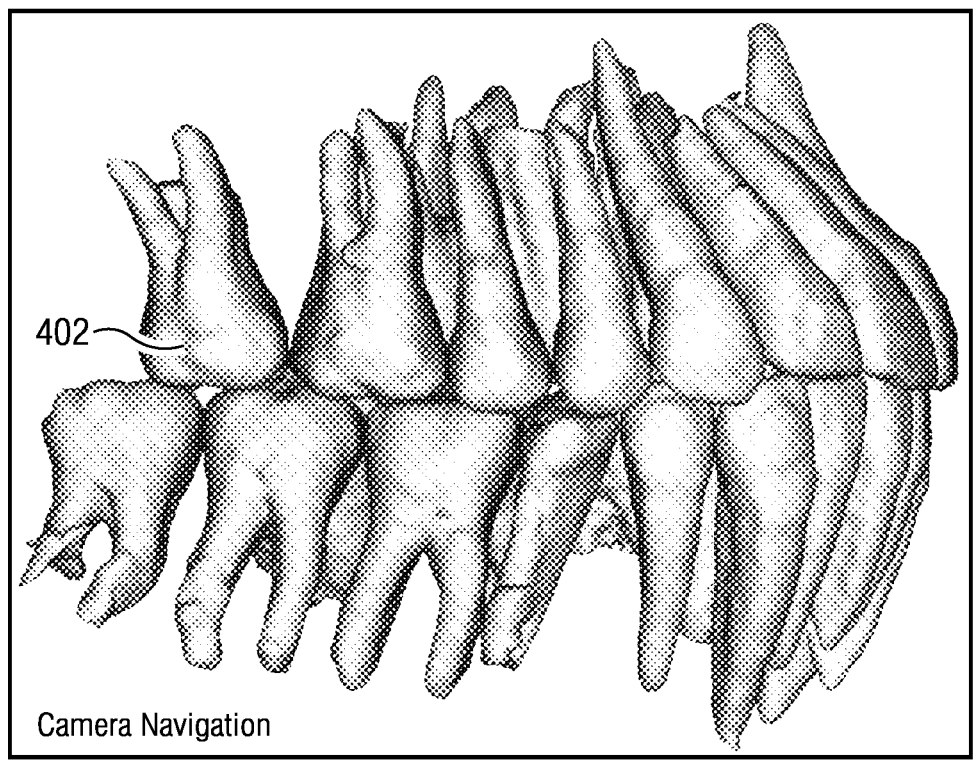

FIG. 11 shows a finished model 402 of the teeth with roots of a patient obtained by registering the mesh data from the surface scan with the mesh data from the volume scan of the dentition of a patient.

Figure 12:
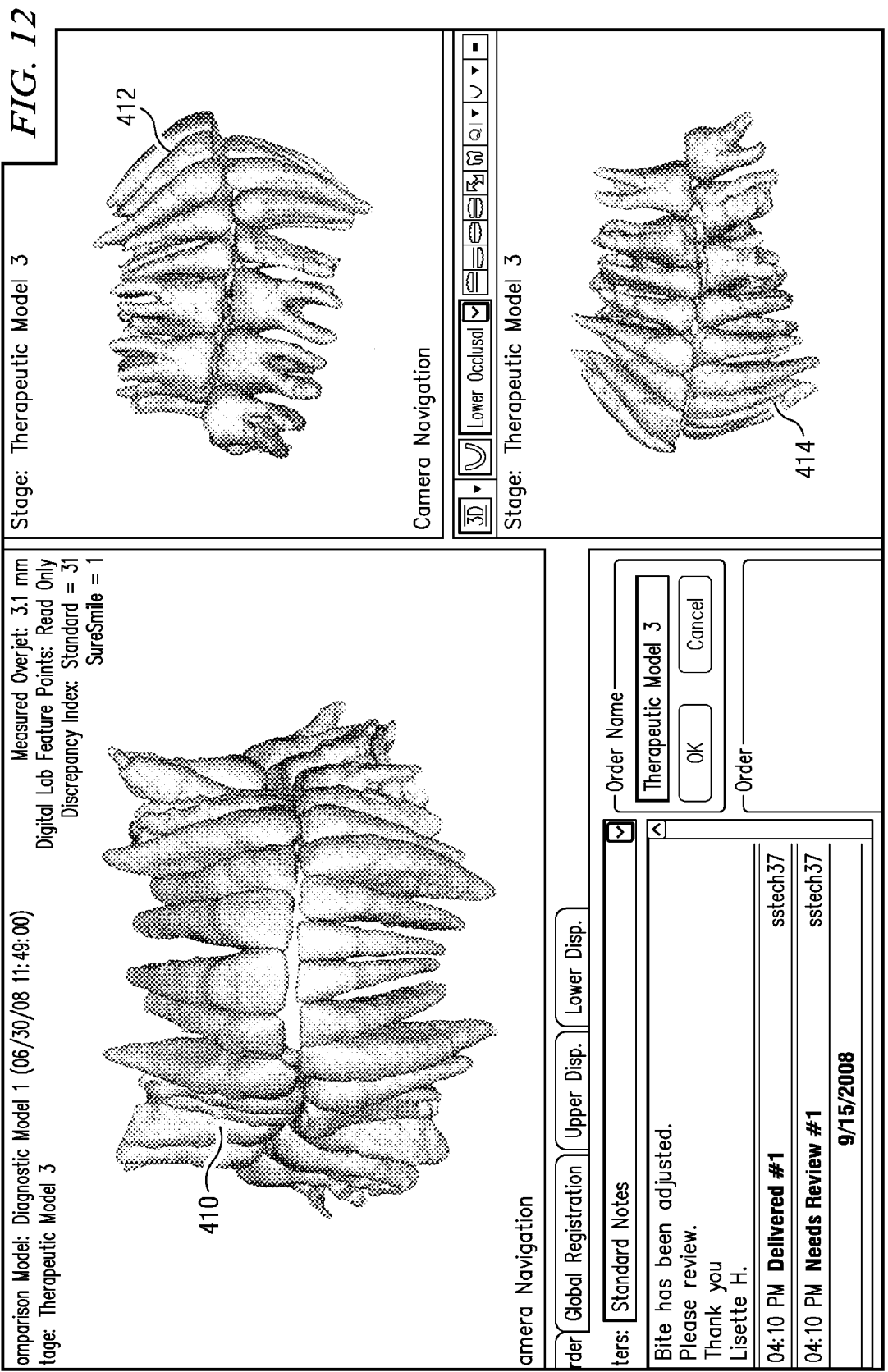
Figure 13:
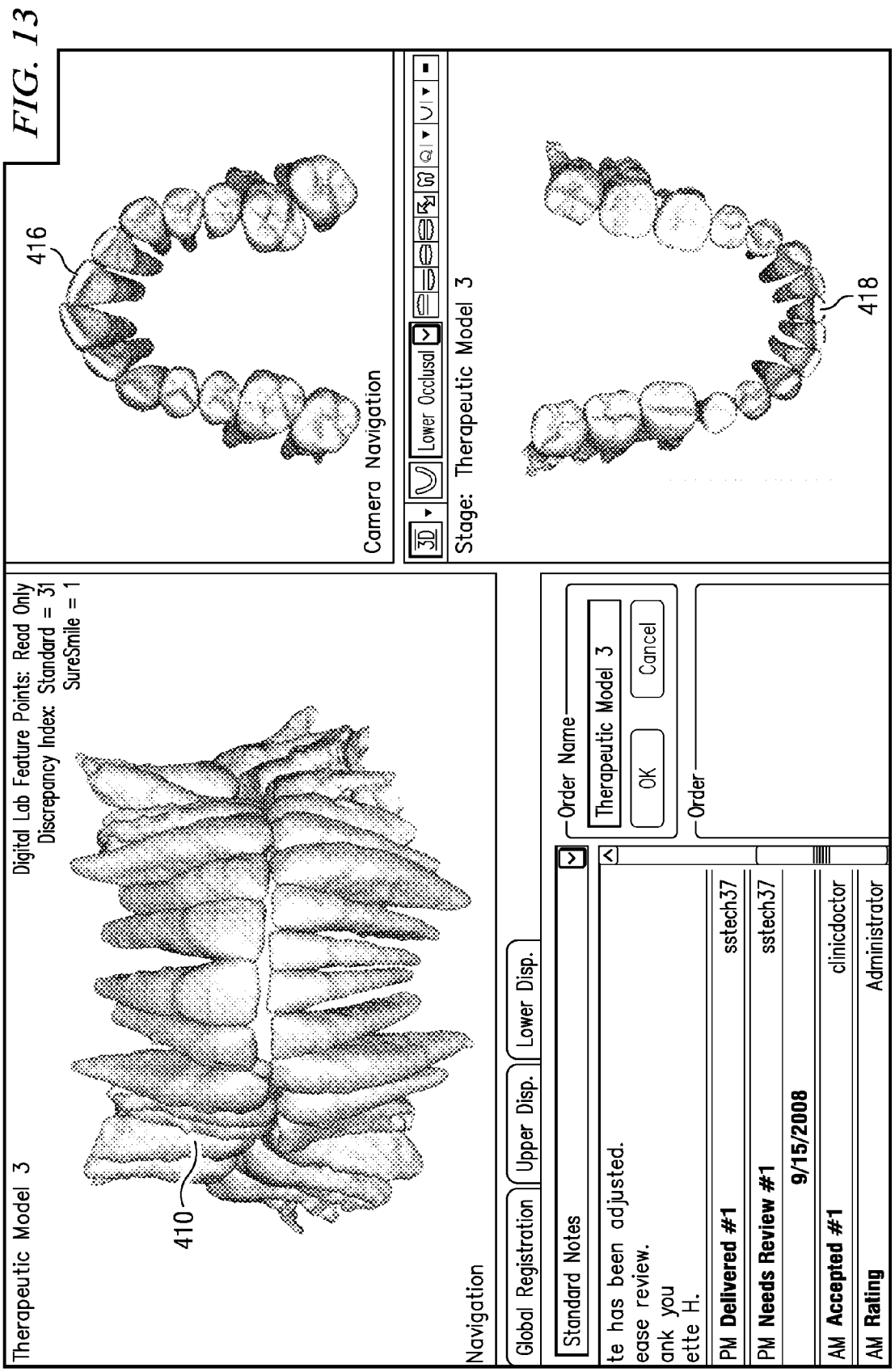

FIGS. 12 and 13 show different views 410, 412, 414, 416 and 418 of the teeth model shown in FIG. 11.

Figure 14:
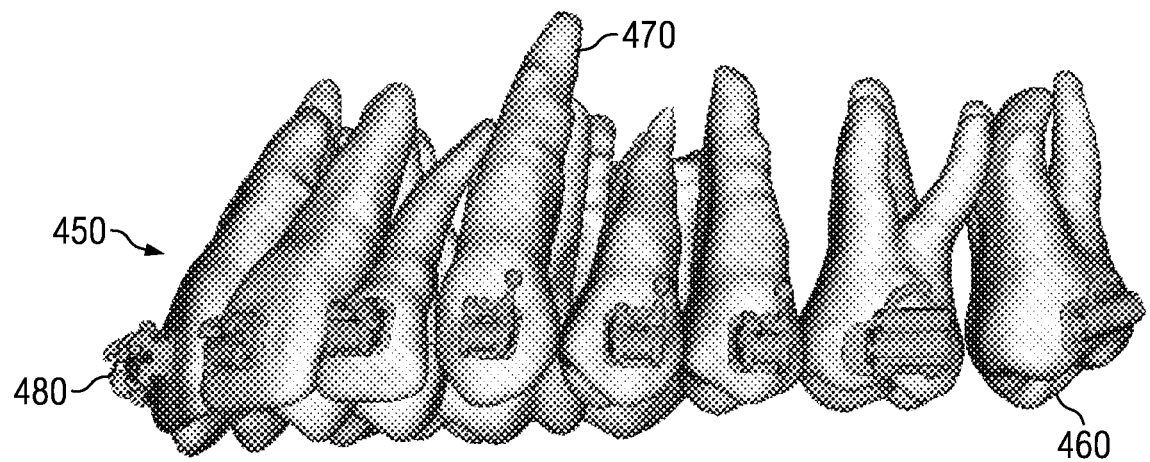
Figure 14:
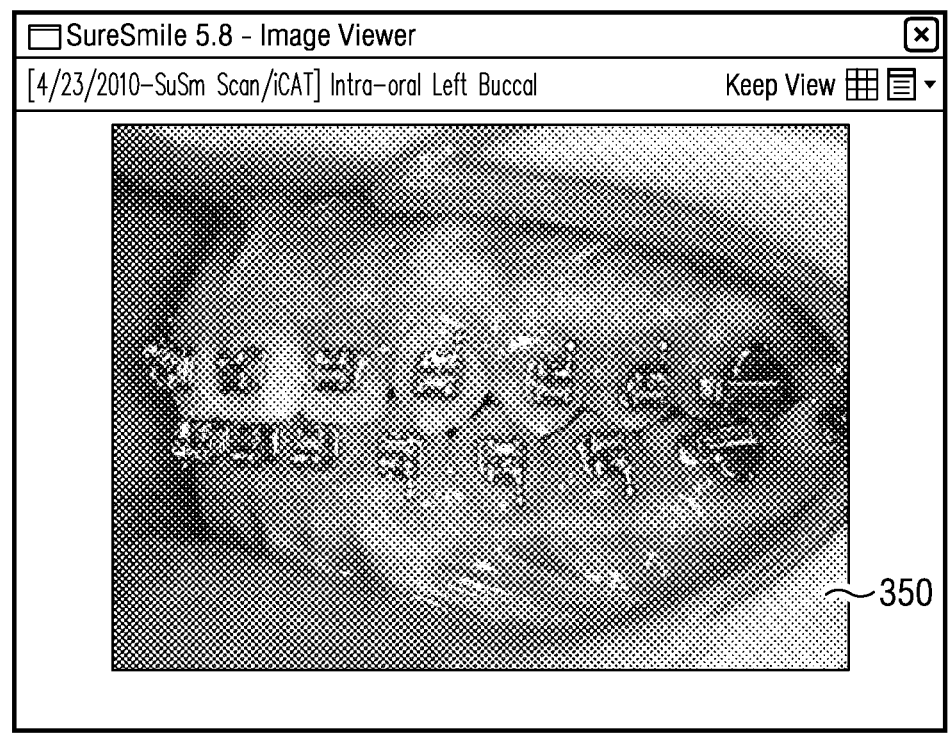

FIG. 14 shows the three-dimensional final model 450 teeth with crowns 460 and roots 470 having brackets 480 placed on the teeth. Also shown in this figure is a photographic view of the mouth 350 of the patient, previously shown in FIG. 10.

The preferred embodiment of the invention combines volume scan data with surface scan data to get the benefit of both and compensate for weaknesses of each.

The advantages of volume scan data are (i). acquisition of invisible data (CBCT & MRT) such as (a) roots, bone, condile, Airways; whereas the advantages of the surface scan data are high accuracy and resolution on visible surfaces.

The disadvantages of volume scan data are (i). side effects of high density material (beam hardening and scattering) (CBCT) such as metal appliances (brackets, tads, etc), metal-crowns and metal fillings, (ii). invisibility of gingiva when there is metal in the patient's mouth, (iii). limited resolution when low dose (CBCT), (iv.) limited resolution (MRT), (v). invisibility of water less material, and (vi.) loss of small features because of noise and low-pass filtering (both CBCT & MRT). On the other hand surface Scan is limited only to visible surfaces such as crowns, gingiva, and appliances such as brackets.

The goal of the invention is to obtain (a.) high accuracy representation of visible areas, especially small features on teeth, (b) representation of gingival, (c) representation of tooth roots, (d) representation of bones, (e) representation of condole, and (f) representation of brackets, all in very high precision 3-D modeling by combining surface scan data with the volume scan data.

In summary, method and workstation for generating three dimensional digital or virtual model of the dentition and surrounding anatomy of a patient from surface scan data and volume scan data are disclosed. Surface scans of a patient's dentition are obtained using in-vivo scanning or other types of scanning such as scanning an impression of the patient's dentition or scanning a physical model of the patient's dentition. Volume scan data of the patient's dentition are obtained using Cone Beam Computed Tomography (CBCT) or Magnetic Resonance Tomography (MRT) imaging equipment. By registering the surface scan data with the volume scan data three dimensional models of a patient's dentition and surrounding anatomy including roots, bones, soft tissues, airways, etc. are obtained.

While presently preferred embodiments of the invention have been described for purposes of illustration of the best mode contemplated by the inventors for practicing the invention, wide variation from the details described herein is foreseen without departure from the spirit and scope of the invention. This true spirit and scope is to be determined by reference to the appended claims. The term "bend", as used in the claims, is interpreted to mean either a simple translation movement of the work-piece in one direction or a twist (rotation) of the work-piece, unless the context clearly indicates otherwise.

The invention claimed is:

1. A method of creating an integrated three-dimensional virtual patient model comprising a patient's dentition and craniofacial anatomical structures using a surface scanner, a volume scanner and a workstation, comprising the steps of:
   (a) obtaining raw three-dimensional surface scanning data of one or more visual portions of said dentition of said patient using said surface scanner;
   (b) obtaining raw three-dimensional volume scanning data of said dentition and craniofacial anatomical structures of said patient using said volume scanner;
   (c) downloading and then processing said raw three-dimensional surface scanning data and said raw three-dimensional volume scanning data in said workstation; and
   (d) registering said surface scanning data after processing with said volume scanning data after processing in said workstation, thereby (i) creating said integrated three-dimensional virtual patient model; and (ii) automatically eliminating noise and/or distortion, if any, from said volume scanning data.

2. The method of claim 1, wherein said one or more visual portions of said dentition are one or more teeth of said patient with surrounding gingiva tissues.

3. The method of claim 2, wherein crowns of said one or more teeth have metal fillings.

4. The method of claim 2, wherein metal brackets are bonded to said one or more teeth.

5. The method of claim 1, wherein said three-dimensional surface scanning data are obtained by in-vivo scanning said patient's dentition using an optical scanner.

6. The method of claim 5, wherein said scanner is non-invasive and works in a reference-independent manner.

7. The method of claim 1, wherein said virtual patient model comprises said patient's teeth with crowns and roots, upper and lower jaw bones, gingiva and soft tissues.

8. The method of claim 1, wherein said step of registering replaces scanned distorted images of said patient's teeth with metal fillings and/or metal brackets in said volume scanning data with corresponding scanned images of said patient's teeth having high accuracy and resolution from said surface scanning data.

9. The method of claim 1, wherein said virtual patient model is further processed to create models of said patient's teeth with crowns and roots.

10. The method of claim 9, wherein said models of said patient's teeth with crowns and roots are further processed so that one or more teeth movements can be simulated in said workstation for planning orthodontic treatment for said patient.

11. A system for creating an integrated three-dimensional virtual patient model comprising a patient's dentition and craniofacial anatomical structures, comprising:
   (a) a surface scanner; wherein raw three-dimensional surface scanning data of one or more visual portions of said dentition of said patient are obtained using said surface scanner;
   (b) a volume scanner; wherein raw three-dimensional volume scanning data of said dentition and craniofacial anatomical structures of said patient are obtained using said volume scanner;
   (c) a workstation; wherein said raw three-dimensional surface scanning data and said raw three-dimensional volume scanning data are downloaded in said workstation; wherein said workstation contains a set of software instructions for processing and then registering said surface scanning data with said volume scanning data, thereby (i) creating said integrated three-dimensional virtual patient model; and (ii) automatically eliminating noise and/or distortion, if any, from said volume scanning data.

12. The system of claim 11, wherein said one or more visual portions of said dentition are one or more teeth of said patient with surrounding gingiva tissues.

13. The system of claim 12, wherein crowns of said one or more teeth have metal fillings.

14. The system of claim 12, wherein metal brackets are bonded to said one or more teeth.

15. The system of claim 11, wherein said surface scanner is an in-vivo, optical scanner.

16. The system of claim 15, wherein said scanner is non-invasive and works in a reference-independent manner.

17. The system of claim 11, wherein said virtual patient model comprises said patient's teeth with crowns and roots, upper and lower jaw bones, gingiva and soft tissues.

18. The system of claim 11, wherein said software instructions in said workstation replace scanned distorted images of said patient's teeth with metal fillings and/or metal brackets in said volume scanning data with corresponding scanned images of said patient's teeth having high accuracy and resolution from said surface scanning data during while registering said surface scanning data with said volume scanning data.

19. The system of claim 11, wherein said virtual patient model is further processed to create models of said patient's teeth with crowns and roots.

20. The system of claim 19, wherein said workstation further contains software instructions for processing models of said patient's teeth with crowns and roots so that one or more teeth movements can be simulated in said workstation for planning orthodontic treatment for said patient.

* * * * *